United States Patent
Mudumba et al.

(10) Patent No.: US 11,285,081 B2
(45) Date of Patent: Mar. 29, 2022

(54) SEALED PREPARATION CONTAINER AND USE FOR SAME

(71) Applicant: SANTEN PHARMACEUTICAL CO., LTD., Osaka (JP)

(72) Inventors: Sreenivasu Mudumba, Emeryville, CA (US); Kedar Datar, Emeryville, CA (US); Hiromitsu Shiono, Ikoma (JP); Chun-jung Chu, Emeryville, CA (US); Le An, San Bruno, CA (US); Sudeep Rauser, Humble, TX (US)

(73) Assignee: SANTEN PHARMACEUTICAL CO., LTD., Osaka (JP)

( * ) Notice: Subject to any disclaimer, the term of this patent is extended or adjusted under 35 U.S.C. 154(b) by 109 days.

(21) Appl. No.: 16/486,490

(22) PCT Filed: Feb. 14, 2018

(86) PCT No.: PCT/JP2018/005051
§ 371 (c)(1),
(2) Date: Aug. 15, 2019

(87) PCT Pub. No.: WO2018/151143
PCT Pub. Date: Aug. 23, 2018

(65) Prior Publication Data
US 2019/0358128 A1      Nov. 28, 2019

Related U.S. Application Data

(60) Provisional application No. 62/460,654, filed on Feb. 17, 2017.

(51) Int. Cl.
| | | |
|---|---|---|
| *A61J 3/00* | (2006.01) | |
| *A61K 31/436* | (2006.01) | |
| *B65D 1/02* | (2006.01) | |
| *A61P 27/14* | (2006.01) | |
| *A61P 27/06* | (2006.01) | |
| *A61P 37/06* | (2006.01) | |
| *B29L 31/00* | (2006.01) | |
| *A61K 45/06* | (2006.01) | |
| *B65D 81/32* | (2006.01) | |
| *A61J 1/20* | (2006.01) | |

(52) U.S. Cl.
CPC ............ *A61J 3/00* (2013.01); *A61K 31/436* (2013.01); *A61P 27/06* (2018.01); *A61P 27/14* (2018.01); *A61P 37/06* (2018.01); *B65D 1/02* (2013.01); *A61J 1/2096* (2013.01); *A61K 45/06* (2013.01); *B29L 2031/7158* (2013.01); *B65D 81/3216* (2013.01)

(58) Field of Classification Search
None
See application file for complete search history.

(56) References Cited

U.S. PATENT DOCUMENTS

| | | | | |
|---|---|---|---|---|
| 8,492,400 | B2 * | 7/2013 | Mudumba | A61P 9/10 |
| | | | | 514/291 |
| 2002/0003122 | A1 * | 1/2002 | Sudo | B65D 1/0261 |
| | | | | 215/247 |
| 2006/0264453 | A1 * | 11/2006 | Mudumba | A61K 47/44 |
| | | | | 514/291 |
| 2007/0203173 | A1 | 8/2007 | Mudumba et al. | |

FOREIGN PATENT DOCUMENTS

| | | |
|---|---|---|
| JP | 2009528276 A | 8/2009 |
| JP | 2016118473 A | 6/2016 |

OTHER PUBLICATIONS

FDA Draft Guidance, "Selection of the Appropriate Package Type Terms and Recommendations for Labeling Injectable Medical Products Packaged in Multiple-Dose, Single-Dose, and Single-Patient-Use Containers for Human Use Guidance for Industry," Oct. 2015 (Year: 2015).*
International Preliminary Report on Patentability dated Aug. 29, 2019, for PCT Patent Application No. PCT/JP2018/005051 filed on Feb. 14, 2018, 9 pages.
International Search Report dated May 15, 2018, for PCT Patent Application No. PCT/JP2018/005051 filed on Feb. 14, 2018, 1 page.
Office Action received for Indian Patent Application No. 201937036611, dated Mar. 31, 2021, 6 pages.

* cited by examiner

*Primary Examiner* — Jeffrey S Lundgren
*Assistant Examiner* — Michael J Schmitt
(74) *Attorney, Agent, or Firm* — Morrison & Foerster LLP

(57) ABSTRACT

In order to enable long-term stabilization of rapamycin contained in a liquid formulation, a formulation sealing vessel of the present invention includes: a sealed vessel body in which a liquid formulation containing 2% (w/w) rapamycin or a salt thereof, 94% (w/w) polyethylene glycol, and 4% (w/w) ethanol is sealed, the sealed vessel body having a volume of 0.1 mL to 1.0 mL, the liquid formulation containing no antioxidant, and the liquid formulation having a total volume of 0.02 mL to 1.0 mL.

16 Claims, 2 Drawing Sheets

SEALED PREPARATION CONTAINER AND USE FOR SAME

CROSS REFERENCE TO RELATED APPLICATIONS

This application is a U.S. national phase application under 35 U.S.C. § 371 of International Application No. PCT/JP2018/005051, filed Feb. 14, 2018, which claims benefit under 35 U.S.C. 119(e) of U.S. Provisional Application No. 62/460,654, filed Feb. 17, 2017, the contents of which are incorporated herein by reference in their entirety for all purposes.

TECHNICAL FIELD

The present invention relates to a formulation sealing vessel and use thereof.

BACKGROUND ART

Rapamycin is a metabolite of *Streptomyces hygroscopicus,* an actinomycete isolated from soil from Easter Island. Rapamycin was discovered in the 1970s as a macroride antibiotic. Thereafter, rapamycin was found to have immunosuppressive functions and was recognized in the United States and Europe as being effective in preventing organ rejection in kidney transplant patients. Rapamycin is now used under the commercial name Rapamune (registered trademark). Rapamycin is known to degrade due to the effects of factors such as temperature when in liquid formulation. For example, Patent Literature 1 discloses techniques for stabilizing rapamycin contained in a liquid formulation.

CITATION LIST

Patent Literature

[Patent Literature 1]
Japanese Translation of PCT International Application, Tokuhyo, No. 2009-528276

SUMMARY OF INVENTION

Technical Problem

Rapamycin is known to degrade due to the effects of factors such as temperature when in liquid formulation, and as such there has been a need to store rapamycin in a frozen state at −20° C. Such storage conditions are not preferable for users (for example, doctors and pharmacists), and frozen storage and shipment are problematic in terms of transporting rapamycin.

An object of an aspect of the present invention is to provide a formulation sealing vessel which enables long-term stabilization of rapamycin contained in a liquid formulation. Another object of an aspect of the present invention is to provide a formulation sealing vessel which enables long-term stabilization of rapamycin contained in a liquid formulation, even in the case of storage under refrigeration at a temperature of 2° C. to 8° C.

Solution to Problem

As a result of diligent study to solve the above problems, the inventors of the present invention discovered that it is possible to achieve long-term stabilization of rapamycin contained in a liquid formulation by use of a formulation sealing vessel including: a sealed vessel body in which a liquid formulation containing 2% (w/w) rapamycin or a salt thereof (hereinafter also referred to simply as "rapamycin"), 94% (w/w) polyethylene glycol, and 4% (w/w) ethanol is sealed, the sealed vessel body having a volume of 0.1 mL to 1.0 mL, the liquid formulation containing no antioxidant, and the liquid formulation having a total volume of 0.02 mL to 1.0 mL. Furthermore, the inventors discovered that the formulation sealing vessel enables long-term stabilization of rapamycin contained in the liquid formulation even in a case where the formulation sealing vessel is stored under refrigeration at a temperature of 2° C. to 8° C.

In other words, a formulation sealing vessel in accordance with an aspect of the present invention includes: a sealed vessel body in which a liquid formulation containing 2% (w/w) rapamycin or a salt thereof, 94% (w/w) polyethylene glycol, and 4% (w/w) ethanol is sealed, the sealed vessel body having a volume of 0.1 mL to 1.0 mL, the liquid formulation containing no antioxidant, and the liquid formulation having a total volume of 0.02 mL to 1.0 mL.

A formulation sealing vessel in accordance with another aspect of the present invention is a formulation sealing vessel including: a sealed vessel body in which a liquid formulation containing 2% (w/w) rapamycin or a salt thereof, 94% (w/w) polyethylene glycol, and 4% (w/w) ethanol is sealed, the sealed vessel body having a volume of 0.1 mL to 1.0 mL, the liquid formulation containing no antioxidant, the liquid formulation having a total volume of 0.02 mL to 1.0 mL, the sealed vessel body having (i) a trunk part having a cylindrical shape and (ii) a bottom part having a conical shape, the conical shape having (i) a vertex which is a point on a central axis of the cylindrical shape of the trunk part and (ii) wall surfaces which are inclined downwardly toward the vertex.

A formulation sealing vessel in accordance with another aspect of the present invention is a formulation sealing vessel including: a sealed vessel body in which a liquid formulation containing 2% (w/w) rapamycin or a salt thereof, 94% (w/w) polyethylene glycol, and 4% (w/w) ethanol is sealed, the liquid formulation containing no antioxidant, the sealed vessel body having (i) a trunk part having a cylindrical shape and (ii) a bottom part having a conical shape, the conical shape having (i) a vertex which is a point on a central axis of the cylindrical shape of the trunk part and (ii) wall surfaces which are inclined downwardly toward the vertex.

A method in accordance with yet another aspect of the present invention is a method of stabilizing a liquid formulation containing 2% (w/w) rapamycin or a salt thereof, 94% (w/w) polyethylene glycol, and 4% (w/w) ethanol, the liquid formulation containing no antioxidant, the method including the step of: sealing the liquid formulation in a sealed vessel body having a volume of 0.1 mL to 1.0 mL, the liquid formulation having a total volume of 0.02 mL to 1.0 mL and containing no antioxidant.

A method in accordance with yet another aspect of the present invention is a method of stabilizing a liquid formulation containing 2% (w/w) rapamycin or a salt thereof, 94% (w/w) polyethylene glycol, and 4% (w/w) ethanol, the liquid formulation containing no antioxidant, the method including the step of: sealing the liquid formulation in a sealed vessel body having (i) a trunk part having a cylindrical shape and (ii) a bottom part having a conical shape, the conical shape having (i) a vertex which is a point on a central axis of the cylindrical shape of the trunk part and (ii) wall surfaces which are inclined downwardly toward the vertex.

A liquid formulation in accordance with yet another aspect of the present invention is a liquid formulation sealed in a sealed vessel body, the liquid formulation containing 2% (w/w) rapamycin or a salt thereof, 94% (w/w) polyethylene glycol, and 4% (w/w) ethanol, the sealed vessel body having a volume of 0.1 mL to 1.0 mL, the liquid formulation containing no antioxidant, the liquid formulation having a total volume of 0.02 mL to 1.0 mL.

A liquid formulation in accordance with yet another aspect of the present invention is a liquid formulation sealed in a sealed vessel body, the liquid formulation containing 2% (w/w) rapamycin or a salt thereof, 94% (w/w) polyethylene glycol, and 4% (w/w) ethanol, the liquid formulation containing no antioxidant, the sealed vessel body having (i) a trunk part having a cylindrical shape and (ii) a bottom part having a conical shape, the conical shape having (i) a vertex which is a point on a central axis of the cylindrical shape of the trunk part and (ii) wall surfaces which are inclined downwardly toward the vertex.

Advantageous Effects of Invention

These aspects of the present invention enable long-term stabilization of rapamycin contained in a liquid formulation. These aspects of the present invention enable long-term stabilization of rapamycin contained in a liquid formulation, even in the case of storage under refrigeration at a temperature of 2° C. to 8° C.

DESCRIPTION OF EMBODIMENTS

Figure 1:
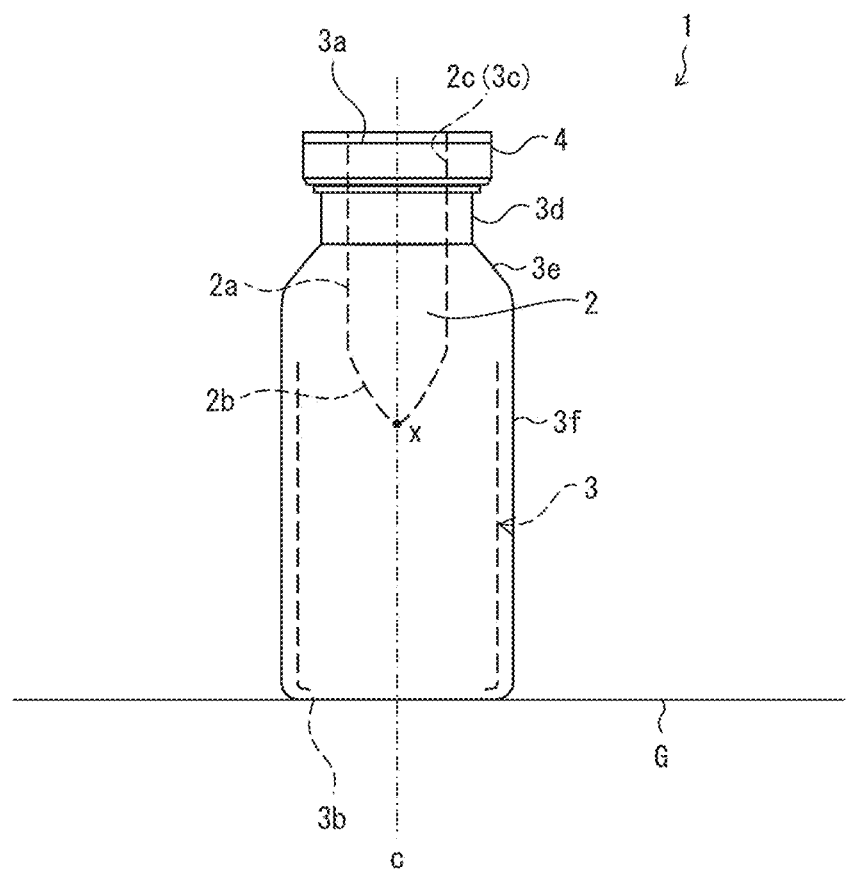
FIG. 1 is a side view illustrating a configuration of a formulation sealing vessel in accordance with an embodiment of the present invention.

The following description will discuss an embodiment of the present invention in detail. Note that "% (w/w)", which may also be expressed as "weight %", refers to a percentage equivalent to the mass (in grams) of an ingredient (active ingredient or additive) contained 100 g of a liquid formulation of the present invention.

(Liquid Formulation Contained in Formulation Sealing Vessel)

A liquid formulation, contained in a sealed vessel body of a formulation sealing vessel in accordance with the present embodiment, contains 2% (w/w) rapamycin or a salt thereof, 94% (w/w) polyethylene glycol, and 4% (w/w) ethanol. It is optional whether or not the liquid formulation contains an antioxidant, but the liquid formulation preferably does not contain an antioxidant.

Rapamycin, which is a compound also known as sirolimus, is a substance represented by the following chemical structural formula.

[Chem. 1]

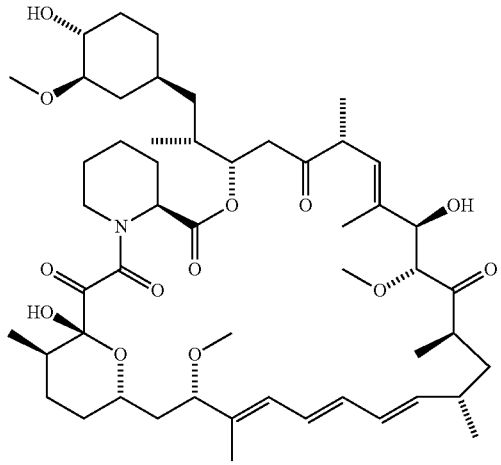

The salt of rapamycin is not particularly limited, provided that it is a salt which is acceptable as a pharmaceutical. Examples of the salt of rapamycin include: a salt formed with an inorganic acid such as hydrochloric acid, hydrobromic acid, hydriodic acid, nitric acid, sulfuric acid, and phosphoric acid; a salt formed with an organic acid such as acetic acid, fumaric acid, maleic acid, succinic acid, citric acid, tartaric acid, adipic acid, gluconic acid, glucoheptonic acid, glucuronic acid, terephthalic acid, methanesulfonic acid, lactic acid, hippuric acid, 1,2-ethanedisulfonic acid, isethionic acid, lactobionic acid, oleic acid, pamoic acid, polygalacturonic acid, stearic acid, tannic acid, trifluoromethanesulfonic acid, benzenesulfonic acid, p-toluenesulfonic acid, lauryl sulfate ester, methyl sulfate, naphthalenesulfonic acid, and sulfosalicylic acid; a quaternary ammonium salt formed with methyl bromide, methyl iodide, or the like; a salt formed with a halogen ion such as a bromine ion, a chlorine ion, and an iodine ion; a salt formed with an alkali metal such as lithium, sodium, and potassium; a salt formed with an alkaline earth metal such as calcium and magnesium; a metal salt formed with iron, zinc, or the like; a salt formed with ammonia; and a salt formed with an organic amine such as triethylenediamine, 2-aminoethanol, 2,2-iminobis(ethanol), 1-deoxy-1-(methylamino)-2-D-sorbitol, 2-amino-2-(hydroxymethyl)-1,3-propanediol, procaine, and N,N-bis(phenylmethyl)-1,2-ethanediamine.

The rapamycin or the salt thereof can be produced in accordance with a normal method in the fields of biochemistry and organic chemistry. A commercially available product can be used as the rapamycin or the salt thereof.

The liquid formulation used in the present embodiment contains 94% (w/w) polyethylene glycol. Polyethylene glycol (hereinafter also referred to as "PEG") is a polyether obtained by polymerization of ethylene glycol. Polyethylene glycol is represented by the chemical structural formula $HO(CH_2CH_2O)_nH$, where n is the degree of polymerization. PEG can be produced in accordance with a normal method in the fields of biochemistry and organic chemistry. A commercially available product can be used as the PEG.

In the present embodiment, the polyethylene glycol has an average molecular weight which is preferably 100 to 2000, more preferably 100 to 1000, even more preferably 100 to 800, even more preferably 200 to 600, and even more preferably 400 to 600, 400 and 600 being particularly preferable, and 400 being most preferable. Specific examples of the polyethylene glycol include polyethylene glycol 100 (PEG 100), polyethylene glycol 200 (PEG 200), polyethylene glycol 300 (PEG 300), polyethylene glycol 400 (PEG 400), polyethylene glycol 600 (PEG 600), and polyethylene glycol 800 (PEG 800). For example, polyethylene glycol 400 refers to a polyethylene glycol whose average molecular weight is approximately 400.

The liquid formulation used in the present embodiment contains 4% (w/w) ethanol. The ethanol can be produced in accordance with a normal method in the fields of biochemistry and organic chemistry. A commercially available product can be used as the ethanol.

The liquid formulation used in the present embodiment preferably does not contain an antioxidant. Examples of such an antioxidant include ascorbic acid, citric acid, sodium sulfite, disodium EDTA, dithiothreitol (DTT), fumaric acid, beta hydroxyanisole (BHA), propyl gallate, alpha and beta tocopherols, toluene sulfonic acid, tartaric acid, thioglycerol, thiourea, sodium formaldehyde sulfoxylate, sodium thiosulfate, glutamic acid, butylated hydroxytoluene (BHT), ascorbyl palmitate, benzyl alcohol, benzalkonium chloride, and maleic acid.

The dosage form of the liquid formulation used in the present embodiment is not particularly limited. Examples thereof include an injection. Preferable examples of the dosage form include an ophthalmic injection, an intraarticular injection, a hypodermic injection, an intramuscular injection, a spinal injection, and an intraventricular injection. More preferable examples of the dosage form include an ophthalmic injection. Particularly preferable examples of the dosage form include an intravitreal injection.

The liquid formulation used in the present embodiment can be administered as necessary in accordance with the dosage form thereof. For example, in the case of an ophthalmic injection, the liquid formulation can be administered intravitreally, into the conjunctival sac, subconjunctivally, as a sub-Tenon's capsule injection, proximal to the posterior sclera, periorbitally, or between the sclera and conjunctiva. For example, in the case of an ophthalmic injection administered intravitreally, a dose is not particularly limited provided that it is an amount sufficient to bring about a desired medicinal effect, but is preferably 1 µL to 100 µL per administration, more preferably 5 µL to 70 µL per administration, even more preferably 8 µL to 60 µL per administration, even more preferably 10 µL to 50 µL per administration, particularly preferably 10 µL, 20 µL, 25 µL, 30 µL, 35 µL, 40 µL, 45 µL, or 50 µL per administration, and most preferably 20 µL per administration.

A dose of rapamycin contained in the liquid formulation used in the present embodiment is preferably 0.001 mg/eye to 30 mg/eye, more preferably 0.01 mg/eye to 10 mg/eye, even more preferably 0.1 mg/eye to 5 mg/eye, even more preferably 0.2 mg/eye to 1.6 mg/eye, particularly preferably 0.2 mg/eye, 0.3 mg/eye, 0.4 mg/eye, 0.5 mg/eye, 0.6 mg/eye, 0.7 mg/eye, 0.8 mg/eye, 1 mg/eye, 1.2 mg/eye, 1.4 mg/eye, or 1.6 mg/eye, and most preferably 0.44 mg/eye.

In a case where the liquid formulation used in the present embodiment is administered intravitreally on a continuous basis, administration frequency is not particularly limited provided that the frequency is sufficient to bring about a desired medicinal effect, but is preferably from once per week to once every 3 years; more preferably once per week, once every 2 weeks, once per month, once every 2 months, once every 3 months, once every 4 months, once every 5 months, once every 6 months, once per year, once every 2 years, or once every 3 years; even more preferably once every 2 months, once every 3 months, once every 4 months, once every 5 months, once every 6 months, or once per year; and most preferably once every 2 months. The administration frequency can be changed as necessary.

The liquid formulation used in the present embodiment is effective as a pharmaceutical and can be used as a drug for preventing or treating an eye disease such as age-related macular degeneration, diabetic retinopathy, retinopathy of prematurity, retinal vein occlusion, retinal artery occlusion, polypoidal choroidal vasculopathy, retinal angiomatous proliferation, myopic choroidal neovascularization, diabetic macular edema, eye neoplasm, radiation retinopathy, iris rubeosis, neovascular glaucoma, proliferative vitreoretinopathy (PVR), keratomycosis, and uveitis. The liquid formulation is preferably used as a drug for preventing or treating uveitis, particularly preferably for posterior segment uveitis, and most preferably for noninfectious posterior segment uveitis.

(Formulation Sealing Vessel)

A formulation sealing vessel in accordance with the present embodiment comprises a sealed vessel body in which the liquid formulation containing the rapamycin is sealed.

The sealed vessel body has, between itself and the liquid formulation sealed therein, a headspace made up of a gas. The liquid formulation is in contact with a headspace gas containing oxygen gas at a ratio of not more than 20%, not more than 19.5%, not more than 19%, not more than 18.5%, not more than 18%, not more than 17.5%, not more than 17%, not more than 16.5%, not more than 16%, not more than 15%, not more than 13%, not more than 11%, not more than 10%, not more than 9%, not more than 7%, not more than 5%, not more than 3%, or not more than 1%. The headspace in the sealed vessel body contains oxygen in an amount of not more than 13 µL, not more than 12 µL, not more than 11 µL, not more than 10 µL, not more than 9 µL, not more than 8 µL, not more than 7 µL, not more than 6 µL, not more than 5 µL, not more than 4 µL, not more than 3 µL, not more than 2 µL, not more than 1.45 µL, not more than 1 µL, not more than 0.75 µL, not more than 0.55 µL, not more than 0.5 µL, not more than 0.25 µL, not more than 0.2 µL, not more than 0.1 µL, not more than 0.09 µL, not more than 0.05 µL, not more than 0.03 µL, not more than 0.01 µL, or not more than 0.001 µL per 1 mg of active agent (rapamycin) in the liquid formulation. The liquid formulation has a concentration (%) of oxygen in dissolved gases of not more than 20%, not more than 19.5%, not more than 19%, not more than 18.5%, not more than 18%, not more than 17.5%, not more than 17%, not more than 16.5%, not more than 16%, not more than 15%, not more than 13%, not more than 11%, not more than 10%, not more than 9%, not more than 7%, not more than 5%, not more than 3%, or not more than 1%.

The headspace gas in contact with the liquid formulation contains an inert gas. Examples of the inert gas include nitrogen and rare gases such as argon and helium. The inert gas is particularly preferably nitrogen. In a case where the inert gas is nitrogen, the headspace gas in contact with the liquid formulation contains more than 80% nitrogen gas, more than 85% nitrogen gas, more than 90% nitrogen gas, more than 95% nitrogen gas, or more than 97% nitrogen gas.

The sealed vessel body has a shape or size that minimizes the headspace relative to the volume of the liquid formulation contained therein. The headspace can be minimized by minimizing the fill volume (that is, the volume) of the sealed vessel body.

The liquid formulation is sealed in the sealed vessel body such that a ratio of the total volume of the liquid formulation to the volume of the headspace is not less than 0.1, not less than 0.2, not less than 0.25, not less than 0.3, not less than 0.4, not less than 0.5, not less than 0.6, not less than 0.7, not less than 0.8, not less than 0.9, not less than 1.0, not less than 1.1, not less than 1.2, not less than 1.3, not less than 1.4, not less than 1.5, not less than 2.0, not less than 2.5, not less than 3.0, not less than 3.5, or not less than 4.0.

The liquid formulation is sealed in the sealed vessel body such that a ratio of the total volume of the liquid formulation to the volume of the sealed vessel body is not less than 0.02, not less than 0.03, not less than 0.04, not less than 0.06, not less than 0.08, not less than 0.1, not less than 0.2, not less than 0.4, not less than 0.6, not less than 0.8, or 1.0.

The sealed vessel body of the formulation sealing vessel in accordance with the present embodiment has a volume that is preferably 0.02 mL to 1.0 mL, more preferably 0.1 mL to 1.0 mL, even more preferably 0.2 mL to 0.9 mL, even more preferably 0.3 mL to 0.7 mL, even more preferably 0.45 mL to 0.55 mL, and particularly preferably 0.5 mL. The liquid formulation sealed in the sealed vessel body has a total volume which is 0.02 mL to 1.0 mL, more preferably 0.1 mL to 0.5 mL, even more preferably 0.1 mL to 0.4 mL, and even more preferably 0.1 mL to 0.3 mL. Specifically, the total volume is, for example, 0.1 mL, 0.2 mL, 0.3 mL, or 0.4 mL, and is particularly preferably 0.2 mL or 0.3 mL. With the formulation sealing vessel in accordance with the present embodiment, it is possible to dramatically increase the length of stabilization of the rapamycin in the liquid formulation by setting the volume of the sealed vessel body and the total volume of the liquid formulation to specific values. For example, the volume of the sealed vessel body and the total volume of the liquid formulation are set preferably such that the volume of the sealed vessel body is 0.1 mL to 1.0 mL and the total volume of the liquid formulation is 0.02 mL to 1.0 mL; more preferably such that the volume of the sealed vessel body is 0.3 mL to 0.7 mL and the total volume of the liquid formulation is 0.1 mL to 0.5 mL; even more preferably such that the volume of the sealed vessel body is 0.5 mL and the total volume of the liquid formulation is 0.1 mL to 0.5 mL; even more preferably such that the volume of the sealed vessel body is 0.5 mL and the total volume of the liquid formulation is 0.1 mL to 0.4 mL; and particularly preferably such that the volume of the sealed vessel body is 0.5 mL and the total volume of the liquid formulation is 0.2 mL or 0.3 mL.

The rapamycin or the salt thereof in the liquid formulation has a residual rate in the sealed vessel body of at least 80%, preferably at least 90%, and more preferably 95% at a temperature of 2° C. to 8° C. over at least 1 month, 3 months, 4 months, 5 months, 6 months, 7 months, 8 months, 9 months, 10 months, 11 months, 12 months, 14 months, 16 months, 18 months, 20 months, 22 months, 24 months, 30 months, or 36 months.

The rapamycin or the salt thereof in the liquid formulation has a residual rate in the sealed vessel body of at least 80%, preferably at least 90%, and more preferably 95% at a temperature of −20° C. over at least 1 month, 3 months, 4 months, 5 months, 6 months, 7 months, 8 months, 9 months, 10 months, 11 months, 12 months, 14 months, 16 months, 18 months, 20 months, 22 months, 24 months, 30 months, or 36 months.

(Method of Stabilizing Liquid Formulation)

A method in accordance with the present embodiment is not particularly limited, provided that it is method of stabilizing a liquid formulation containing 2% (w/w) rapamycin or a salt thereof, 94% (w/w) polyethylene glycol, and 4% (w/w) ethanol, the method including the step of: sealing the liquid formulation in a sealed vessel body having a volume of 0.1 mL to 1.0 mL, the liquid formulation having a total volume of 0.02 mL to 1.0 mL. It is optional whether or not the liquid formulation contains an antioxidant, but the liquid formulation preferably does not contain an antioxidant.

The above method enables long-term stable storage of rapamycin contained in a liquid formulation, under refrigeration at a temperature of at least 2° C. to 8° C., even in a case where no antioxidant is used.

(Liquid Formulation)

A liquid formulation in accordance with the present embodiment is not particularly limited, provided that it is a liquid formulation sealed in a sealed vessel body, the liquid formulation containing 2% (w/w) rapamycin or a salt thereof, 94% (w/w) polyethylene glycol, and 4% (w/w) ethanol, the sealed vessel body having a volume of 0.1 mL to 1.0 mL, the liquid formulation having a total volume of 0.02 mL to 1.0 mL. It is optional whether or not the liquid formulation contains an antioxidant, but the liquid formulation preferably does not contain an antioxidant.

The above method enables long-term stable storage of rapamycin contained in a liquid formulation, under refrigeration at a temperature of at least 2° C. to 8° C., even in a case where no antioxidant is used.

(Configuration of Formulation Sealing Vessel)

Figure 2:
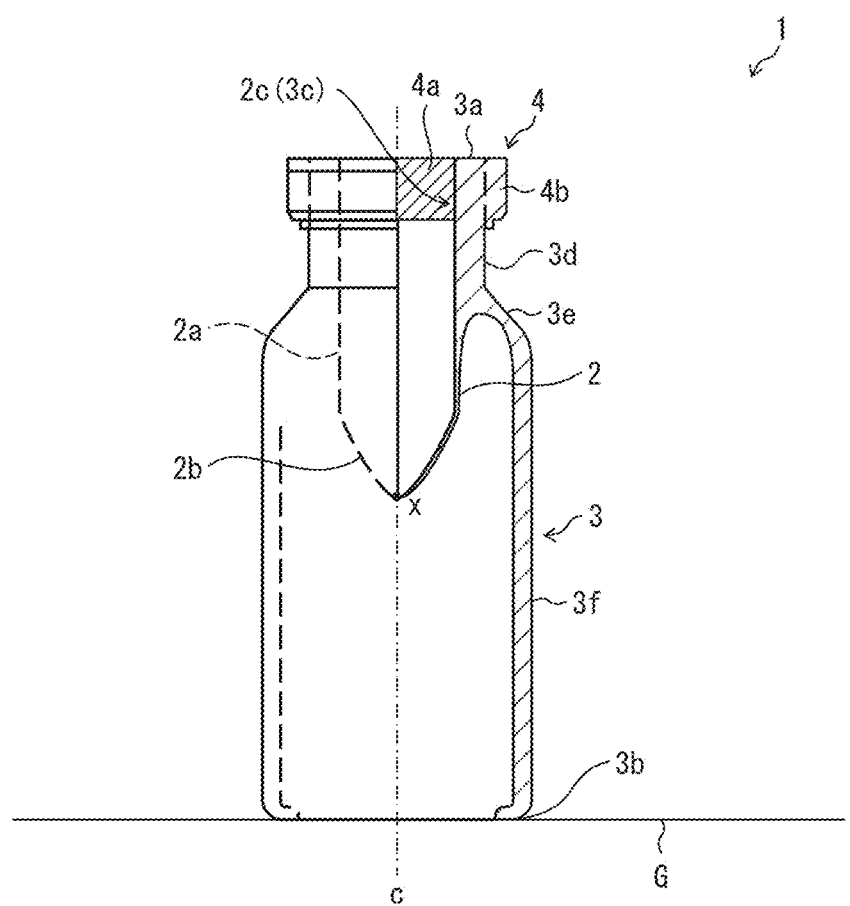
FIG. 2 is a partial cross-sectional view illustrating a formulation sealing vessel in accordance with an embodiment of the present invention.

FIG. 1 is a side view illustrating a configuration of a formulation sealing vessel 1 in accordance with the present embodiment. FIG. 2 is a partial cross-sectional view illustrating the formulation sealing vessel 1 in accordance with the present embodiment. FIGS. 1 and 2 illustrate the formulation sealing vessel 1 in a state where it is provided on a plane G.

As illustrated in FIGS. 1 and 2, the formulation sealing vessel 1 includes a sealed vessel body 2 in which the liquid formulation is sealed, a support section 3 for supporting the sealed vessel body 2, and a stopper section 4 for sealing the liquid formulation inside the sealed vessel body 2.

The sealed vessel body 2 has a trunk part 2a having a cylindrical shape and a bottom part 2b having a conical shape. A material from which the sealed vessel body 2 is made is not particularly limited. Possible examples include glass or resins such as polyethylene. Note that herein, a trunk part 2a side of the sealed vessel body 2 is considered to be an upper side, and a bottom part 2b side is considered to be a lower side. An opening 2c is formed at an upper end part of the sealed vessel body 2, that is, at upper end part of the trunk part 2a. A lower end part of the sealed vessel body 2 (that is, a lower end part of the bottom part 2b) does not have an opening. The conical shape of the bottom part 2b of the sealed vessel body 2 has a vertex X which is a point on a central axis C of the cylindrical shape of the trunk part 2a. The conical shape of the bottom part 2b has wall surfaces which are inclined downwardly toward the vertex X.

The support section 3 is a hollow structure in which an upper end 3a of the support section 3 and a lower end 3b of the support section 3 each have an opening. A material from which the support section 3 is made is not particularly limited. Possible examples of the material include glass or resins such as polyethylene. The support section 3 has a vial shape in which the opening 3c of the upper end 3a is smaller than the opening of the lower end 3b. Herein, "vial shape" refers to the shape of a typical vial for containing an injection solution. More specifically, the support section 3 having the vial shape has (i) a smaller diameter cylindrical part 3d whose diameter is equivalent to the diameter of the opening 3c of the upper end 3a and (ii) a larger diameter cylindrical part 3f whose diameter is equivalent to the diameter of the opening of the lower end 3b. The smaller diameter cylindrical part 3d and the larger diameter cylindrical part 3f are formed continuously along a vertical direction so as to have the same central axis C. The smaller diameter cylindrical part 3d and the larger diameter cylindrical part 3f are joined by a shoulder part 3e whose surface is inclined downwardly and outwardly from the central axis C.

The opening 2c of the sealed vessel body 2 is the same opening as the opening 3c of the upper end 3a of the support section 3. A side wall of the trunk part 2a of the sealed vessel body 2 is at least partially joined to an inner wall of the smaller diameter cylindrical part 3d of the support section 3. The bottom part 2b of the sealed vessel body 2 is contained in the larger diameter cylindrical part 3f of the support section 3. The vertex X of the bottom part 2b is spaced from the lower end 3b of the support section 3. As such, when the formulation sealing vessel 1 is placed such that the lower end 3b of the support section 3 contacts the plane G, the vertex X of the bottom part 2b of the sealed vessel body 2 is positioned so as to be opposite to the plane G.

The stopper section 4 includes (i) a rubber stopper 4a for sealing an upper end of the sealed vessel body 2 and (ii) a holding member 4b which holds the rubber stopper 4a so as to prevent the rubber stopper 4a from coming off. Once the rubber stopper 4a has been fully pushed into the opening 2c of the sealed vessel body 2, the rubber stopper 4a is in complete contact with an inner wall of the trunk part 2a. This makes it possible to seal the sealed vessel body 2.

The liquid formulation in the sealed vessel body 2 of the formulation sealing vessel 1 is withdrawn and then injected into a human by use of a syringe. The syringe used for withdrawing and injecting the liquid formulation includes: a withdrawal needle for withdrawing the liquid formulation sealed in the sealed vessel body 2; an injection needle for injecting, into a human body, the liquid formulation withdrawn by the withdrawal needle; and a syringe barrel configured to connect to both the withdrawal needle and the injection needle. Discussed next is a method of using the formulation sealing vessel 1 having the above-described configuration.

First, a withdrawal syringe, for withdrawing the liquid formulation sealed in the sealed vessel body 2 of the formulation sealing vessel 1, is prepared. Specifically, the withdrawal syringe is assembled by connecting the withdrawal needle and the syringe barrel.

Next, the withdrawal needle of the withdrawal syringe is inserted into the rubber stopper 4a of the formulation sealing vessel 1 so as to pass therethrough. Then, a plunger provided in the syringe barrel is pulled away from the formulation sealing vessel 1 so as to draw into the syringe barrel the liquid formulation in the sealed vessel body 2.

Thereafter, the withdrawal needle of the withdrawal syringe is replaced with the injection needle. The liquid formulation contained in the syringe barrel is then injected into a human body via the injection needle.

Note here that the volume of the sealed vessel body 2 is 0.1 mL to 1.0 mL, and the total volume of the liquid formulation sealed in the sealed vessel body 2 is 0.02 mL to 1.0 mL. In a typical configuration of a vial whose liquid formulation fill volume is 0.1 mL to 1.0 mL, the dimensions of the vial are extremely small. Because of this, when the vial is placed on the plane G, it is difficult for the person preparing the injection to hold the vial and withdraw the liquid formulation using the withdrawal syringe. In order to address this issue, the formulation sealing vessel 1 in accordance with the present embodiment has the support section 3 which supports the sealed vessel body 2 so that the bottom part 2b of the sealed vessel body 2 faces the plane G on which to place the formulation sealing vessel 1 and is spaced from the plane G. The support section 3 supports the sealed vessel body 2 such that it is spaced from the plane G. This allows a person preparing the injection to easily hold the formulation sealing vessel 1 while it is placed on the plane G and use the withdrawal syringe to withdraw the liquid formulation sealed in the sealed vessel body 2, even if the dimensions of the sealed vessel body 2 are extremely small.

The length of the support section 3 (the distance from the plane G to the upper end 3a) is not particularly limited, provided that the length allows the person preparing the injection to easily hold the formulation sealing vessel 1 and use the withdrawal syringe to withdraw the liquid formulation sealed in the sealed vessel body 2. The length of the support section 3 is, for example, preferably not less than 1 cm, more preferably 1 cm to 10 cm, even more preferably 1 cm to 5 cm, even more preferably 2 cm to 5 cm, and particularly preferably 3 cm to 5 cm.

The sealed vessel body 2 has the trunk part 2a having the cylindrical shape and the bottom part 2b having the conical shape. The conical shape of the bottom part 2b has a vertex X, which is a point on the central axis C of the cylindrical shape of the trunk part 2a, and wall surfaces which are inclined downwardly toward the vertex X. Due to this configuration, when the person preparing the injection uses the withdrawal syringe to withdraw the liquid formulation, the inclination of the wall surfaces of the conical shape causes the withdrawal needle to be positioned at the vertex X when the withdrawal needle contacts the bottom part 2b. This makes it possible to stably withdraw the liquid formulation.

As described above, the support section 3 is shaped like a typical vial. This allows the person preparing the injection to, for example, use the withdrawal syringe to withdraw the liquid formulation while holding the smaller diameter cylindrical part 3d of the support section 3, in the same manner as with a normal vial. This improves handleability during withdrawal of the liquid formulation. Note that the shape of the support section 3 need only be a vial shape that facilitates withdrawal. Examples of the vial shape include, for example, the shape of a vial having a fill volume of 2 mL.

Furthermore, because the support section 3 has the shape of a typical vial, a filling apparatus for filling liquid formulations into typical vials can be used to fill the liquid formulation into the formulation sealing vessel 1. This improves versatility with respect to filling apparatuses for filling the liquid formulation.

(Formulation Transfer Kit and Formulation Transfer Packaging Body)

A formulation transfer kit in accordance with the present embodiment is a kit for transferring a liquid formulation containing 2% (w/w) rapamycin or a salt thereof, 94% (w/w) polyethylene glycol, and 4% (w/w) ethanol. The formulation transfer kit includes, for example: the formulation sealing vessel 1 illustrated in FIG. 1; a withdrawal needle for withdrawing the liquid formulation sealed in the sealed vessel body 2; an injection needle for injecting, into a human body, the liquid formulation withdrawn by the withdrawal needle; and a syringe barrel configured to connect to each of the withdrawal needle and the injection needle. Such a kit including the formulation sealing vessel 1 improves the convenience of the formulation sealing vessel 1 for a user thereof. The formulation transfer kit may include a package insert explaining pharmaceutical products relating to the formulation sealing vessel of an embodiment of the present invention.

A formulation transfer packaging body in accordance with the present embodiment is a packaging body for packaging the formulation transfer kit. The packaging body includes a refrigerant for keeping the formulation transfer kit cool. The formulation transfer packaging body having the refrigerant makes it possible to transfer the liquid formulation containing rapamycin in a manner so as to improve the stability of the liquid formulation. Examples of the refrigerant include dry ice. The formulation transfer packaging body may have printed thereon storage conditions (for example, "storable for 6 weeks at 2° C. to 8° C.") of the formulation transfer kit.

The configuration and positioning of the refrigerant are not particularly limited, provided that the refrigerant keeps the formulation transfer kit cool. For example, in a case where the formulation transfer kit is contained in a first box, the formulation transfer packaging body in accordance with the present embodiment may include a second box for containing the first box. In such a configuration, the refrigerant can be, for example, position in the second box so as to contact a lower surface of the first box.

The present invention is not limited to the embodiments, but can be altered by a skilled person in the art within the scope of the claims. The present invention also encompasses, in its technical scope, any embodiment derived by combining technical means disclosed in differing embodiments. Further, it is possible to form a new technical feature by combining the technical means disclosed in the respective embodiments.

[Recap]

A formulation sealing vessel in accordance with Aspect 1 of the present invention is a formulation sealing vessel including: a sealed vessel body in which a liquid formulation containing 2% (w/w) rapamycin or a salt thereof, 94% (w/w) polyethylene glycol, and 4% (w/w) ethanol is sealed, the sealed vessel body having a volume of 0.1 mL to 1.0 mL, the liquid formulation containing no antioxidant, and the liquid formulation having a total volume of 0.02 mL to 1.0 mL.

The above aspect enables long-term stable storage of rapamycin contained in a liquid formulation, under refrigeration at a temperature of at least 2° C. to 8° C., and without the use of an antioxidant.

In Aspect 2 of the present invention, the formulation sealing vessel of Aspect 1 is preferably arranged such that a ratio of the total volume of the liquid formulation to the volume of the sealed vessel body is not less than 0.02.

In Aspect 3 of the present invention, the formulation sealing vessel of Aspect 1 is preferably arranged such that the formulation sealing vessel is stored at a temperature of 2° C. to 8° C.

In Aspect 4 of the present invention, the formulation sealing vessel of Aspect 1 is preferably arranged such that the formulation sealing vessel is stored at a temperature of −20° C.

In Aspect 5 of the present invention, the formulation sealing vessel of Aspect 1 is preferably arranged such that the sealed vessel body has a volume of 0.3 mL to 0.7 mL.

In Aspect 6 of the present invention, the formulation sealing vessel of Aspect 1 is preferably arranged such that the sealed vessel body has a volume of 0.5 mL.

In Aspect 7 of the present invention, the formulation sealing vessel of Aspect 1 is preferably arranged such that the liquid formulation has a total volume of 0.1 mL to 0.5 mL.

In Aspect 8 of the present invention, the formulation sealing vessel of Aspect 1 is preferably arranged such that the liquid formulation has a total volume of 0.1 mL to 0.4 mL.

In Aspect 9 of the present invention, the formulation sealing vessel of Aspect 1 is preferably arranged such that the liquid formulation has a total volume of 0.1 mL to 0.3 mL.

In Aspect 10 of the present invention, the formulation sealing vessel of Aspect 1 is preferably arranged such that the liquid formulation has a total volume of 0.2 mL or 0.3 mL.

In Aspect 11 of the present invention, the formulation sealing vessel of any one of Aspects 1 to 10 can be arranged such that: the sealed vessel body has (i) a trunk part having a cylindrical shape and (ii) a bottom part having a conical shape; and the conical shape has (i) a vertex which is a point on a central axis of the cylindrical shape of the trunk part and (ii) wall surfaces which are inclined downwardly toward the vertex.

With the above configuration, when a person preparing an injection uses a withdrawal syringe to withdraw the liquid formulation, the inclination of the wall surfaces of the conical shape causes a withdrawal needle to be positioned at the vertex when the withdrawal needle contacts the bottom part. This makes it possible to stably withdraw the liquid formulation.

In Aspect 12 of the present invention, the formulation sealing vessel of any one of Aspects 1 to 11 can be arranged so as to further include: a support section configured to support the sealed vessel body so that the bottom part of the sealed vessel body faces a plane on which to place the formulation sealing vessel and is spaced from the plane on which to place the formulation sealing vessel.

With the above configuration, the support section supports the sealed vessel body such that it is spaced from the plane. This allows a person preparing the injection to easily hold the formulation sealing vessel while it is placed on the plane and use a withdrawal syringe to withdraw the liquid formulation sealed in the sealed vessel body, even if the dimensions of the sealed vessel body are extremely small.

In Aspect 13 of the present invention, the formulation sealing vessel of Aspect 12 is preferably arranged such that: the support section has a hollow structure in which an upper end of the support section and a lower end of the support section each have an opening, and the support section has a vial shape in which the opening of the upper end is smaller than the opening of the lower end; and the sealed vessel body has an opening that is the same opening as the opening of the upper end of the support section.

With the above configuration, the support section has a vial shape as described above. This allows a person preparing the injection to, for example, use the withdrawal syringe to withdraw the liquid formulation while holding the opening of the upper end of the support section, in the same manner as with a normal vial. This improves handleability during withdrawal of the liquid formulation.

A formulation sealing vessel in accordance with Aspect 14 of the present invention is a formulation sealing vessel including: a sealed vessel body in which a liquid formulation containing 2% (w/w) rapamycin or a salt thereof, 94% (w/w) polyethylene glycol, and 4% (w/w) ethanol is sealed, the sealed vessel body having a volume of 0.1 mL to 1.0 mL, the liquid formulation containing no antioxidant, the liquid formulation having a total volume of 0.02 mL to 1.0 mL, the sealed vessel body having (i) a trunk part having a cylindrical shape and (ii) a bottom part having a conical shape, the conical shape having (i) a vertex which is a point on a central axis of the cylindrical shape of the trunk part and (ii) wall surfaces which are inclined downwardly toward the vertex.

The above configuration enables long-term stable storage of rapamycin contained in a liquid formulation, under refrigeration at a temperature of at least 2° C. to 8° C., and without the use of an antioxidant. The above configuration also makes it possible to stably withdraw the liquid formulation.

A formulation sealing vessel in accordance with Aspect 15 of the present invention is a formulation sealing vessel including: a sealed vessel body in which a liquid formulation containing 2% (w/w) rapamycin or a salt thereof, 94% (w/w) polyethylene glycol, and 4% (w/w) ethanol is sealed, the liquid formulation containing no antioxidant, the sealed vessel body having (i) a trunk part having a cylindrical shape and (ii) a bottom part having a conical shape, the conical shape having (i) a vertex which is a point on a central axis of the cylindrical shape of the trunk part and (ii) wall surfaces which are inclined downwardly toward the vertex.

The above configuration makes it possible to stably withdraw the liquid formulation.

In Aspect 16 of the present invention, the formulation sealing vessel of any one of Aspects 1 to 15 is preferably arranged such that the liquid formulation is in contact with an inert gas.

In Aspect 17 of the present invention, the formulation sealing vessel of Aspect 16 is preferably arranged such that the inert gas is nitrogen.

In Aspect 18 of the present invention, the formulation sealing vessel of Aspect 1, 14, or 15 is preferably arranged such that the polyethylene glycol is PEG 400.

In Aspect 19 of the present invention, the formulation sealing vessel of any one of Aspects 1 to 18 is preferably arranged such that the rapamycin or the salt thereof has a residual rate of at least 90% over at least 1 month at a temperature of 2° C. to 8° C.

In Aspect 20 of the present invention, the formulation sealing vessel of any one of Aspects 1 to 18 is preferably arranged such that the rapamycin or the salt thereof has a residual rate of at least 90% over at least 3 months at a temperature of 2° C. to 8° C.

In Aspect 21 of the present invention, the formulation sealing vessel of any one of Aspects 1 to 18 is preferably arranged such that the rapamycin or the salt thereof has a residual rate of at least 90% over at least 6 months at a temperature of 2° C. to 8° C.

In Aspect 22 of the present invention, the formulation sealing vessel of any one of Aspects 1 to 18 is preferably arranged such that the rapamycin or the salt thereof has a residual rate of at least 90% over at least 9 months at a temperature of 2° C. to 8° C.

In Aspect 23 of the present invention, the formulation sealing vessel of any one of Aspects 1 to 18 is preferably arranged such that the rapamycin or the salt thereof has a residual rate of at least 90% over at least 12 months at a temperature of 2° C. to 8° C.

In Aspect 24 of the present invention, the formulation sealing vessel of any one of Aspects 1 to 18 is preferably arranged such that the rapamycin or the salt thereof has a residual rate of at least 90% over at least 18 months at a temperature of 2° C. to 8° C.

In Aspect 25 of the present invention, the formulation sealing vessel of any one of Aspects 1 to 18 is preferably arranged such that the rapamycin or the salt thereof has a residual rate of at least 90% over at least 24 months at a temperature of 2° C. to 8° C.

A formulation transfer kit in accordance with Aspect 26 of the present invention is a formulation transfer kit for transferring a liquid formulation containing 2% (w/w) rapamycin or a salt thereof, 94% (w/w) polyethylene glycol, and 4% (w/w) ethanol, the liquid formulation containing no antioxidant, the formulation transfer kit including: a formulation sealing vessel of any one of Aspects 1 to 25; a withdrawal needle for withdrawing the liquid formulation contained in the sealed vessel body; an injection needle for injecting, into a human body, the liquid formulation withdrawn by the withdrawal needle; and a syringe barrel configured to connect to each of the withdrawal needle and the injection needle.

A formulation transfer packaging body in accordance with Aspect 27 of the present invention is a formulation transfer packaging body for packaging a formulation transfer kit of Aspect 26, the formulation transfer packaging body including: a refrigerant for keeping the formulation transfer kit cool.

A method in accordance with Aspect 28 of the present invention is a method of stabilizing a liquid formulation containing 2% (w/w) rapamycin or a salt thereof, 94% (w/w) polyethylene glycol, and 4% (w/w) ethanol, the liquid formulation containing no antioxidant, the method including the step of: sealing the liquid formulation in a sealed vessel body having a volume of 0.1 mL to 1.0 mL, the liquid formulation having a total volume of 0.02 mL to 1.0 mL and containing no antioxidant.

A method in accordance with Aspect 29 of the present invention is a method of stabilizing a liquid formulation containing 2% (w/w) rapamycin or a salt thereof, 94% (w/w) polyethylene glycol, and 4% (w/w) ethanol, the liquid formulation containing no antioxidant, the method including the step of: sealing the liquid formulation in a sealed vessel body having (i) a trunk part having a cylindrical shape and (ii) a bottom part having a conical shape, the conical shape having (i) a vertex which is a point on a central axis of the cylindrical shape of the trunk part and (ii) wall surfaces which are inclined downwardly toward the vertex.

A liquid formulation in accordance with Aspect 30 of the present invention is a liquid formulation sealed in a sealed vessel body, the liquid formulation containing 2% (w/w) rapamycin or a salt thereof, 94% (w/w) polyethylene glycol, and 4% (w/w) ethanol, the sealed vessel body having a volume of 0.1 mL to 1.0 mL, the liquid formulation containing no antioxidant, the liquid formulation having a total volume of 0.02 mL to 1.0 mL.

A liquid formulation in accordance with Aspect 31 of the present invention is a liquid formulation sealed in a sealed vessel body, the liquid formulation containing 2% (w/w) rapamycin or a salt thereof, 94% (w/w) polyethylene glycol, and 4% (w/w) ethanol, the liquid formulation containing no antioxidant, the sealed vessel body having (i) a trunk part having a cylindrical shape and (ii) a bottom part having a conical shape, the conical shape having (i) a vertex which is a point on a central axis of the cylindrical shape of the trunk part and (ii) wall surfaces which are inclined downwardly toward the vertex.

The above aspects enable long-term stable storage of rapamycin contained in a liquid formulation, under refrigeration at a temperature of at least 2° C. to 8° C., and without the use of an antioxidant.

A formulation sealing vessel in accordance with Aspect 32 of the present invention is a formulation sealing vessel including: a sealed vessel body in which a liquid formulation containing 1% (w/w) to 5% (w/w) rapamycin or a salt thereof is sealed, the sealed vessel body having a volume of 0.1 mL to 1.0 mL, the liquid formulation having a total volume of 0.02 mL to 1.0 mL.

In Aspect 33 of the present invention, the formulation sealing vessel of Aspect 32 may be arranged such that the liquid formulation contains an antioxidant.

In Aspect 34 of the present invention, the formulation sealing vessel of Aspect 32 is preferably arranged such that a ratio of the total volume of the liquid formulation to the volume of the sealed vessel body is not less than 0.02.

In Aspect 35 of the present invention, the formulation sealing vessel of Aspect 32 is preferably arranged such that the formulation sealing vessel is stored at a temperature of 2° C. to 8° C.

In Aspect 36 of the present invention, the formulation sealing vessel of Aspect 32 is preferably arranged such that the formulation sealing vessel is stored at a temperature of −20° C.

In Aspect 37 of the present invention, the formulation sealing vessel of Aspect 32 is preferably arranged such that the sealed vessel body has a volume of 0.3 mL to 0.7 mL.

In Aspect 38 of the present invention, the formulation sealing vessel of Aspect 32 is preferably arranged such that the sealed vessel body has a volume of 0.5 mL.

In Aspect 39 of the present invention, the formulation sealing vessel of Aspect 32 is preferably arranged such that the liquid formulation has a total volume of 0.1 mL to 0.5 mL.

In Aspect 40 of the present invention, the formulation sealing vessel of Aspect 32 is preferably arranged such that the liquid formulation has a total volume of 0.1 mL to 0.4 mL.

In Aspect 41 of the present invention, the formulation sealing vessel of Aspect 32 is preferably arranged such that the liquid formulation has a total volume of 0.1 mL to 0.3 mL.

In Aspect 42 of the present invention, the formulation sealing vessel of Aspect 32 is preferably arranged such that the liquid formulation has a total volume of 0.2 mL or 0.3 mL.

In Aspect 43 of the present invention, the formulation sealing vessel of any one of Aspects 32 to 42 is may be arranged such that: the sealed vessel body has (i) a trunk part having a cylindrical shape and (ii) a bottom part having a conical shape; and the conical shape has (i) a vertex which is a point on a central axis of the cylindrical shape of the trunk part and (ii) wall surfaces which are inclined downwardly toward the vertex.

In Aspect 44 of the present invention, the formulation sealing vessel of any one of Aspects 32 to 43 may be arranged so as to further include: a support section configured to support the sealed vessel body so that the bottom part of the sealed vessel body faces a plane on which to place the formulation sealing vessel and is spaced from the plane on which to place the formulation sealing vessel.

In Aspect 45 of the present invention, the formulation sealing vessel of Aspect 44 is preferably arranged such that: the support section has a hollow structure in which an upper end of the support section and a lower end of the support section each have an opening, and the support section has a vial shape in which the opening of the upper end is smaller than the opening of the lower end; and the sealed vessel body has an opening that is the same opening as the opening of the upper end of the support section.

A formulation sealing vessel in accordance with Aspect 46 of the present invention is a formulation sealing vessel including: a sealed vessel body in which a liquid formulation containing 1% (w/w) to 5% (w/w) rapamycin or a salt thereof is sealed, the sealed vessel body having a volume of 0.1 mL to 1.0 mL, the liquid formulation having a total volume of 0.02 mL to 1.0 mL, the sealed vessel body having (i) a trunk part having a cylindrical shape and (ii) a bottom part having a conical shape, the conical shape having (i) a vertex which is a point on a central axis of the cylindrical shape of the trunk part and (ii) wall surfaces which are inclined downwardly toward the vertex.

A formulation sealing vessel in accordance with Aspect 47 of the present invention is a formulation sealing vessel including: a sealed vessel body in which a liquid formulation containing 1% (w/w) to 5% (w/w) rapamycin or a salt thereof is sealed, the sealed vessel body having (i) a trunk part having a cylindrical shape and (ii) a bottom part having a conical shape, the conical shape having (i) a vertex which is a point on a central axis of the cylindrical shape of the trunk part and (ii) wall surfaces which are inclined downwardly toward the vertex.

In Aspect 48 of the present invention, the formulation sealing vessel of any one of Aspects 32 to 47 is preferably arranged such that the liquid formulation is in contact with an inert gas.

In Aspect 49 of the present invention, the formulation sealing vessel of Aspect 48 is preferably arranged such that the inert gas is nitrogen.

In Aspect 50 of the present invention, the formulation sealing vessel of Aspect 32, 46, or 47 is preferably arranged such that the polyethylene glycol is PEG 400.

In Aspect 51 of the present invention, the formulation sealing vessel of any one of Aspects 32 to 50 is preferably arranged such that the rapamycin or the salt thereof has a residual rate of at least 90% over at least 1 month at a temperature of 2° C. to 8° C.

In Aspect 52 of the present invention, the formulation sealing vessel of any one of Aspects 32 to 50 is preferably arranged such that the rapamycin or the salt thereof has a residual rate of at least 90% over at least 3 months at a temperature of 2° C. to 8° C.

In Aspect 53 of the present invention, the formulation sealing vessel of any one of Aspects 32 to 50 is preferably arranged such that the rapamycin or the salt thereof has a residual rate of at least 90% over at least 6 months at a temperature of 2° C. to 8° C.

In Aspect 54 of the present invention, the formulation sealing vessel of any one of Aspects 32 to 50 is preferably arranged such that the rapamycin or the salt thereof has a residual rate of at least 90% over at least 9 months at a temperature of 2° C. to 8° C.

In Aspect 55 of the present invention, the formulation sealing vessel of any one of Aspects 32 to 50 is preferably arranged such that the rapamycin or the salt thereof has a residual rate of at least 90% over at least 12 months at a temperature of 2° C. to 8° C.

In Aspect 56 of the present invention, the formulation sealing vessel of any one of Aspects 32 to 50 is preferably arranged such that the rapamycin or the salt thereof has a residual rate of at least 90% over at least 18 months at a temperature of 2° C. to 8° C.

In Aspect 57 of the present invention, the formulation sealing vessel of any one of Aspects 32 to 50 is preferably arranged such that the rapamycin or the salt thereof has a residual rate of at least 90% over at least 24 months at a temperature of 2° C. to 8° C.

A formulation transfer kit in accordance with Aspect 58 of the present invention is a formulation transfer kit for transferring a liquid formulation containing 1% (w/w) to 5% (w/w) rapamycin or a salt thereof, the formulation transfer kit including: a formulation sealing vessel of any one of Aspects 32 to 57; a withdrawal needle for withdrawing the liquid formulation contained in the sealed vessel body; an injection needle for injecting, into a human body, the liquid formulation withdrawn by the withdrawal needle; and a syringe barrel configured to connect to each of the withdrawal needle and the injection needle.

A formulation transfer packaging body in accordance with Aspect 59 of the present invention is a formulation transfer packaging body for packaging a formulation transfer kit of Aspect 58, the formulation transfer packaging body including: a refrigerant for keeping the formulation transfer kit cool.

A method in accordance with Aspect 60 of the present invention is a method of stabilizing a liquid formulation containing 1% (w/w) to 5% (w/w) rapamycin or a salt thereof, the method including the step of: sealing the liquid formulation in a sealed vessel body having a volume of 0.1 mL to 1.0 mL, the liquid formulation having a total volume of 0.02 mL to 1.0 mL.

A method in accordance with Aspect 61 of the present invention is a method of stabilizing a liquid formulation containing 1% (w/w) to 5% (w/w) rapamycin or a salt thereof, the method including the step of: sealing the liquid formulation in a sealed vessel body having (i) a trunk part having a cylindrical shape and (ii) a bottom part having a conical shape, the conical shape having (i) a vertex which is a point on a central axis of the cylindrical shape of the trunk part and (ii) wall surfaces which are inclined downwardly toward the vertex.

A liquid formulation in accordance with Aspect 62 of the present invention is a liquid formulation sealed in a sealed vessel body, the liquid formulation containing 1% (w/w) to 5% (w/w) rapamycin or a salt thereof, the sealed vessel body having a volume of 0.1 mL to 1.0 mL, the liquid formulation having a total volume of 0.02 mL to 1.0 mL.

A liquid formulation in accordance with Aspect 63 of the present invention is a liquid formulation sealed in a sealed vessel body, the liquid formulation containing 1% (w/w) to 5% (w/w) rapamycin or a salt thereof, the sealed vessel body having (i) a trunk part having a cylindrical shape and (ii) a bottom part having a conical shape, the conical shape having (i) a vertex which is a point on a central axis of the cylindrical shape of the trunk part and (ii) wall surfaces which are inclined downwardly toward the vertex.

EXAMPLES

The following description will discuss the present invention in greater detail, with reference to Examples and a Comparative Example. Note that the present invention is not limited to these Examples.

(Preparation of Rapamycin-Containing Solution)

Rapamycin was dissolved into 100% ethanol by sonication. This produced a rapamycin-ethanol solution, to which PEG 400 was added. Excess ethanol was removed via forced evaporation. Final concentrations as a percentage of the anal formulation weight were as follows. Rapamycin: 2% (w/w); ethanol: 4% (w/w); and PEG 400: 94% (w/w). The solution was sterilized by filtration through a 0.2 micron filter. Note that Super Refined PEG 400 (SR-PEG 400) was used as the PEG 400.

Example 1

The rapamycin-containing solution (amount: 0.3 mL) produced as above was filled into the formulation sealing vessel 1 (volume of sealed vessel body: 0.5 mL) in accordance with the present embodiment. The gas of the headspace was replaced with nitrogen, and thereafter, HPLC was used to analyze change over time of the residual rate (%) of the rapamycin at −20° C. and at 5° C.

Results are indicated in Table 1. As can be seen from Table 1, after 6, 9, 12, 18, 24 and 36 months at −20° C., the rapamycin had a residual rate, relative to the starting amount of rapamycin in the formulation, of 100.0%, 100.4%, 99.7%, 101.4%, 102.4%, and 99.5%, respectively.

Furthermore, in Example 1, after 1, 3, 6, 9, and 12 months at 5° C., the rapamycin had a residual rate, relative to the starting amount of rapamycin in the formulation, of 100.2%, 98.1%, 98.4%, 97.2%, and 97.3%, respectively.

Comparative Example 1

Analysis of change over time of the residual rate (%) of the rapamycin at −20° C. and at 5° C. was carried out in the same manner as Example 1, except that the rapamycin-containing solution (amount: 0.3 mL) produced as above was filled into a typical 2 mL vial having a cylindrical shape.

Results are indicated in Table 1. As can be seen from Table 1, in the case of 0.3 mL of formulation filled into the 2 mL vial, after 4, 6, 9, 12, 18, 24, 30, and 36 months at −20° C., the rapamycin had a residual rate, relative to the starting amount of rapamycin in the formulation, of 97.5%, 96.6%, 97.1%, 98.4%, 96.3%, 97.1%, 97.3%, and 97.0%, respectively.

Furthermore, in Comparative Example 1, after 1, 2, 3, and 6 months at 5° C., the rapamycin had a residual rate, relative to the starting amount of rapamycin in the formulation, of 97.1%, 94.4%, 86.5%, and 54.9%, respectively.

A comparison of the respective residual rates of the rapamycin in Example 1 and Comparative Example 1 as seen in Table 1 shows that both Example 1 and Comparative Example 1 exhibited similar stability of rapamycin stored at −20° C. However, with regards to storage at 5° C., in Example 1, the residual rate of rapamycin after 6 months was approximately twice that of Comparative Example 1. This shows that in Example 1, the stability of rapamycin stored at 5° C. is remarkably improved in comparison to Comparative Example 1.

This demonstrates that Example 1 enables long-term stable storage of rapamycin contained in a liquid formulation, under refrigeration at a temperature of at least 2° C. to 8° C., and without the use of an antioxidant.

TABLE 1

|  | Example 1 | | Comparative Example 1 | | |
|---|---|---|---|---|---|
| Vessel | Formulation sealing vessel 1 | | Vial vessel | | |
| Total volume of liquid formulation | 0.3 mL | | 0.3 mL | | |
| Volume of sealed vessel body | 0.5 mL (Volume of sealed vessel body) | | 2 mL | | |
| Residual rate (%) | −20° C. | $T_0$ 100.3 | −20° C. | $T_0$ | 97.8 |
|  |  |  |  | $T_{4\,m}$ | 97.5 |
|  |  | $T_{6\,m}$ 100.0 |  | $T_{6\,m}$ | 96.6 |
|  |  | $T_{9\,m}$ 100.4 |  | $T_{9\,m}$ | 97.1 |
|  |  | $T_{12\,m}$ 99.7 |  | $T_{12\,m}$ | 98.4 |
|  |  | $T_{18\,m}$ 101.4 |  | $T_{18\,m}$ | 96.3 |
|  |  | $T_{24\,m}$ 102.4 |  | $T_{24\,m}$ | 97.1 |
|  |  |  |  | $T_{30\,m}$ | 97.3 |
|  |  | $T_{36\,m}$ 99.5 |  | $T_{36\,m}$ | 97.0 |
|  | 5° C. | $T_{1\,m}$ 100.2 | 5° C. | $T_{1\,m}$ | 97.1 |
|  |  |  |  | $T_{2\,m}$ | 94.4 |

TABLE 1-continued

|  | Example 1 |  | Comparative Example 1 |  |
|---|---|---|---|---|
|  | $T_{3m}$ | 98.1 | $T_{3m}$ | 86.5 |
|  | $T_{6m}$ | 98.4 | $T_{6m}$ | 54.9 |
|  | $T_{9m}$ | 97.2 |  |  |
|  | $T_{12m}$ | 97.3 |  |  |

Examples 2 to 4

The rapamycin-containing solution (amount: 0.3 mL) produced as above was filled into the formulation sealing vessel 1 (volume of sealed vessel body: 0.5 mL) in accordance with the present embodiment. The gas of the headspace was replaced with nitrogen, and thereafter, HPLC was used to analyze change over time of the residual rate (%) of the rapamycin at 5° C.

Results are indicated in Table 2. These results indicate that Examples 2 to 4 enable at least 18 months of stable storage of rapamycin contained in a liquid formulation, under refrigeration at a temperature of at least 2° C. to 8° C., and without the use of an antioxidant.

TABLE 2

|  | Example 2 |  | Example 3 |  | Example 4 |  |
|---|---|---|---|---|---|---|
| Vessel | Formulation sealing vessel 1 |  |  |  |  |  |
| Total volume of liquid formulation | 0.3 mL |  |  |  |  |  |
| Volume of vessel body | 0.5 mL (Volume of sealed vessel body) |  |  |  |  |  |
| Residual rate (%) | 5° C. $T_0$ | 100.1 | 5° C. $T_0$ | 98.3 | 5° C. $T_0$ | 100.8 |
|  | $T_{3m}$ | 98.7 | $T_{3m}$ | 98.9 | $T_{3m}$ | 101.0 |
|  | $T_{6m}$ | 96.5 | $T_{6m}$ | 96.8 | $T_{6m}$ | 97.1 |
|  | $T_{9m}$ | 95.9 | $T_{9m}$ | 96.9 | $T_{9m}$ | 97.7 |
|  | $T_{12m}$ | 96.1 | $T_{12m}$ | 97.6 | $T_{12m}$ | 99.4 |
|  | $T_{18m}$ | 95.0 | $T_{18m}$ | 96.2 | $T_{18m}$ | 95.4 |

INDUSTRIAL APPLICABILITY

An embodiment of the present invention can be applied to techniques using a liquid formulation containing rapamycin.

REFERENCE SIGNS LIST

1 Formulation sealing vessel
2 Sealed vessel body
2a Trunk part
2b Bottom part
2c, 3c Opening
3 Support section
3a Upper end
3b Lower end
3d Smaller diameter cylindrical part
3e Shoulder part
3f Larger diameter cylindrical part
4 Stopper section
4a Rubber stopper
4b Holding member

The invention claimed is:

1. A formulation sealing vessel comprising:
a sealed vessel body in which a liquid formulation containing 2% (w/w) rapamycin or a salt thereof, 94% (w/w) polyethylene glycol, and 4% (w/w) ethanol is sealed, and
a support section configured to support the sealed vessel body so that a bottom part of the sealed vessel body faces a plane on which to place the formulation sealing vessel and is spaced from the plane on which to place the formulation sealing vessel, wherein:
the sealed vessel body has a volume of 0.1 mL to 1.0 mL;
the liquid formulation contains no antioxidant;
the liquid formulation has a total volume of 0.02 mL to 1.0 mL;
the support section has a hollow structure in which an upper end of the support section and a lower end of the support section each have an opening, and the support section has a vial shape in which the opening of the upper end is smaller than the opening of the lower end; and
the sealed vessel body has an opening that is the same opening as the opening of the upper end of the support section.

2. The formulation sealing vessel according to claim 1, wherein a ratio of the total volume of the liquid formulation to the volume of the sealed vessel body is not less than 0.02.

3. The formulation sealing vessel according to claim 1, wherein the sealed vessel body has a volume of 0.3 mL to 0.7 mL.

4. The formulation sealing vessel according to claim 1, wherein the sealed vessel body has a volume of 0.5 mL.

5. The formulation sealing vessel according to claim 1, wherein the liquid formulation has a total volume of 0.1 mL to 0.5 mL.

6. The formulation sealing vessel according to claim 1, wherein the liquid formulation has a total volume of 0.1 mL to 0.3 mL.

7. The formulation sealing vessel according to claim 1, wherein:
the sealed vessel body has (i) a trunk part having a cylindrical shape and (ii) a bottom part having a conical shape; and
the conical shape has (i) a vertex which is a point on a central axis of the cylindrical shape of the trunk part and (ii) wall surfaces which are inclined downwardly toward the vertex.

8. The formulation sealing vessel of claim 1, wherein
the sealed vessel body having (i) a trunk part having a cylindrical shape and (ii) a bottom part having a conical shape,
the conical shape having (i) a vertex which is a point on a central axis of the cylindrical shape of the trunk part and (ii) wall surfaces which are inclined downwardly toward the vertex.

9. A formulation sealing vessel comprising:
a sealed vessel body in which a liquid formulation containing 2% (w/w) rapamycin or a salt thereof, 94%

(w/w) polyethylene glycol, and 4% (w/w) ethanol is sealed, the liquid formulation containing no antioxidant, and a support section configured to support the sealed vessel body so that a bottom part of the sealed vessel body faces a plane on which to place the formulation sealing vessel and is spaced from the plane on which to place the formulation sealing vessel, wherein:

the sealed vessel body has (i) a trunk part having a cylindrical shape and (ii) a bottom part having a conical shape;

the conical shape has (i) a vertex which is a point on a central axis of the cylindrical shape of the trunk part and (ii) wall surfaces which are inclined downwardly toward the vertex;

the support section has a hollow structure in which an upper end of the support section and a lower end of the support section each have an opening, and the support section has a vial shape in which the opening of the upper end is smaller than the opening of the lower end; and the sealed vessel body has an opening that is the same opening as the opening of the upper end of the support section.

10. The formulation sealing vessel according claim 1, wherein the liquid formulation is in contact with an inert gas.

11. The formulation sealing vessel according to claim 10, wherein the inert gas is nitrogen.

12. The formulation sealing vessel according to claim 1, wherein the polyethylene glycol is PEG 400.

13. A formulation transfer kit for transferring a liquid formulation containing 2% (w/w) rapamycin or a salt thereof, 94% (w/w) polyethylene glycol, and 4% (w/w) ethanol, the liquid formulation containing no antioxidant, the formulation transfer kit comprising:

a formulation sealing vessel recited in claim 1;

a withdrawal needle for withdrawing the liquid formulation contained in the sealed vessel body;

an injection needle for injecting, into a human body, the liquid formulation withdrawn by the withdrawal needle; and a syringe barrel configured to connect to each of the withdrawal needle and the injection needle.

14. A formulation transfer packaging body for packaging a formulation transfer kit recited in claim 13, the formulation transfer packaging body comprising:

a refrigerant for keeping the formulation transfer kit cool.

15. A method of stabilizing a liquid formulation containing 2% (w/w) rapamycin or a salt thereof, 94% (w/w) polyethylene glycol, and 4% (w/w) ethanol, the liquid formulation containing no antioxidant, the method comprising the step of:

sealing the liquid formulation in a sealed vessel body having a volume of 0.1 mL to 1.0 mL, the liquid formulation having a total volume of 0.02 mL to 1.0 mL and containing no antioxidant, wherein:

the sealed vessel comprises a support section configured to support the sealed vessel body so that a bottom part of the sealed vessel body faces a plane on which to place the formulation sealing vessel and is spaced from the plane on which to place the formulation sealing vessel;

the support section has a hollow structure in which an upper end of the support section and a lower end of the support section each have an opening, and the support section has a vial shape in which the opening of the upper end is smaller than the opening of the lower end; and the sealed vessel body has an opening that is the same opening as the opening of the upper end of the support section.

16. A method of stabilizing a liquid formulation containing 2% (w/w) rapamycin or a salt thereof, 94% (w/w) polyethylene glycol, and 4% (w/w) ethanol, the liquid formulation containing no antioxidant, the method comprising the step of:

sealing the liquid formulation in a sealed vessel body having (i) a trunk part having a cylindrical shape and (ii) a bottom part having a conical shape, wherein:

the sealed vessel comprises a support section configured to support the sealed vessel body so that a bottom part of the sealed vessel body faces a plane on which to place the formulation sealing vessel and is spaced from the plane on which to place the formulation sealing vessel;

the support section has a hollow structure in which an upper end of the support section and a lower end of the support section each have an opening, and the support section has a vial shape in which the opening of the upper end is smaller than the opening of the lower end;

the sealed vessel body has an opening that is the same opening as the opening of the upper end of the support section; and the conical shape having (i) a vertex which is a point on a central axis of the cylindrical shape of the trunk part and (ii) wall surfaces which are inclined downwardly toward the vertex.

* * * * *